United States Patent [19]

Ipenburg

[11] Patent Number: 5,791,896
[45] Date of Patent: Aug. 11, 1998

[54] APPARATUS AND METHOD FOR PROVIDING A DENTAL AID ON TEETH

[75] Inventor: Alexander Gerrit Ipenburg, Dordrecht, Netherlands

[73] Assignee: Aptus B.V., Papendrecht, Netherlands

[21] Appl. No.: 765,233

[22] PCT Filed: Jun. 14, 1995

[86] PCT No.: PCT/NL95/00210

§ 371 Date: Feb. 27, 1997

§ 102(e) Date: Feb. 27, 1997

[87] PCT Pub. No.: WO95/34250

PCT Pub. Date: Dec. 21, 1995

[30] Foreign Application Priority Data

Jun. 14, 1994 [NL] Netherlands .................. 9400968

[51] Int. Cl.⁶ ............................................ A61C 3/00
[52] U.S. Cl. ................................................ 433/3; 433/24
[58] Field of Search ............................... 433/3, 24, 37; 601/164

[56] References Cited

U.S. PATENT DOCUMENTS

| | | | |
|---|---|---|---|
| 2,311,158 | 2/1943 | Conway et al. | 433/37 |
| 3,738,005 | 6/1973 | Cohen et al. | 433/3 |
| 3,787,976 | 1/1974 | Cohen | 433/3 |
| 4,183,141 | 1/1980 | Dellinger et al. | 433/3 |
| 4,224,710 | 9/1980 | Solow | 601/164 |
| 5,055,038 | 10/1991 | Ronay et al. | 433/24 |

*Primary Examiner*—John J. Wilson
*Attorney, Agent, or Firm*—Merchant, Gould, Smith, Edell, Welter & Schmidt, P.A.

[57] ABSTRACT

The invention relates to an apparatus for providing a dental aid (18) on at least one tooth (7) of at least one row of teeth (2), which apparatus comprises a mold (1) containing the impression of at least a portion of a number of teeth from a row, pressure means (3,4,5) being connected with the mold which comprises fastening means (5) for the dental aid and are adapted to move the dental aid in a controlled manner from a first position to a second position.

9 Claims, 3 Drawing Sheets

5,791,896

1

APPARATUS AND METHOD FOR PROVIDING A DENTAL AID ON TEETH

The invention relates to an apparatus for providing a dental aid on at least one tooth of at least one row of teeth, which apparatus comprises a mold containing the impression of at least a portion of a number of teeth from a row.

Such an apparatus is known from U.S. Pat. No. 3,738,005. For manufacturing this known apparatus, the dental aids, in this case a number of brackets, are temporarily bonded at the desired locations on a model of the row of teeth, whereupon the mold is formed on this model with aids. When the finished mold is removed, the temporary bond of the brackets comes loose, as a result of which the brackets are left in the mold. After the brackets have been provided with a bonding agent, the mold is placed over the row of teeth and held in this position until the bonding agent has cured and the brackets are thus fixed on the row of teeth. After removal of the mold, leaving the brackets behind, the wire or brace desired for a dental treatment can be arranged through the brackets.

The advantage of employing such an apparatus is that the proper position of the brackets can be determined and fixed outside the patient's mouth and even in his absence, while the positioning of the brackets on the row of teeth takes place in a quick and accurately determined manner. However, this manner of operating may give rise to problems, because when the mold with brackets provided with bonding agent is slid onto the row of teeth, bonding agent will be scraped from these brackets and spread across the tooth. Even more disadvantageous, however, is the fact that due or not due to scraping, air bubbles become enclosed between the bonding agent and the tooth, become enclosed air bubbles may cause dental carries, which, however, only appears when, in the course of time, the brackets are removed.

U.S. Pat. No. 4,183,141 discloses a method and an apparatus for providing a number of aids on a number of teeth of a set of teeth. According to the known method, a cast is made of a set of teeth, in a known manner, first in negative and then in positive. Then, the different teeth are out loose from the positive cast made and placed in a soft plastic medium such as wax, while they are positioned in an ideal position. This means that the loose teeth are placed in the positions which, in the opinion of the dentist, orthodontist, patient or dental technician, the teeth would have to assume after use of the brace to be formed with the brackets. The thus formed idealized model of the set of teeth is accurately disposed on a table so that the whole is plane within a curved supporting block slightly spaced therefrom. On the supporting block, a number of guide blocks are placed, corresponding to the desired number of brackets, in such a manner that a fastening lip extends above the relevant tooth while a guide passage extends at a desired height and at a desired angle relative to the tooth face on which the bracket is to be provided. Over the teeth a synthetic mold is formed wherein impressions of the upper edges of the different teeth will be made and wherein the fastening lips are fixedly received. The mold is out into sections, each section carrying one guide block. The sections of the mold are then positioned, one by one, on the relevant tooth in the set of teeth to be treated. Then, on an end of a sliding element that is slideable in the guide passage, a bracket is mounted having its base surface facing the tooth face, and next each bracket is provided with cement and placed on the relevant tooth by pressing the sliding element.

An apparatus manufactured according to this known method consists of a series of parts of a mold, each part carrying a guide part. Each part can separately be placed on the relevant tooth irrespective of the position of the tooth at the moment of placing. This enables the apparatus to be reused for the relevant patient, for instance for repositioning a bracket that has come loose during use. However, this known method has the drawback that the teeth have to be cut loose from the model and repositioned individually, and that the position of the teeth should be determined particularly accurately. This means that this method is time-consuming and requires a very high degree of craftsmanship, which renders the method expensive. Moreover, all parts of the apparatus should be placed separately, which renders the apparatus and method even more costly and moreover increases the risk of positioning errors. A further drawback of this known method is that for each patient an entirely new apparatus should be manufactured, so that relatively much labor and material is lost.

The object of the invention is to improve an apparatus of the type mentioned in the opening paragraph such that the above-described problems no longer occur. In accordance with the invention, this object is realized by an apparatus characterized by the features according to claim 1.

Through these features, the dental aids with the bonding agent provided thereon can be brought into a completely withdrawn position, allowing the apparatus to be slid onto the row of teeth without the risk that the bonding agent is scraped off. After this positioning, the pressure means are activated, as a result of which each dental aid is pressed against a tooth. As the direction of displacement is substantially perpendicular to the tooth, air that can be pulled along in an advancing movement and become enclosed, is effectively forced out sideways, which minimizes the chances of air bubbles between bonding agent and tooth. Moreover, this manner of moving and pressing down promotes an optimum bonding of each dental aid to a tooth.

In view of the fact that, typically, a number of dental aids are to be provided on a row or on both rows of teeth of a set of teeth, in accordance with a further embodiment of the invention it is preferred to provide a series of pressure means that can at least partly be activated together. It is observed that it is also possible to position the dental aids consecutively by sliding the mold in place and removing it a number of times.

In a preferred embodiment of an apparatus according to the invention, the fastening means comprise at least a deformable fastening element that is fixedly connectable with the pressure means, while at least one dental aid can be positioned on the fastening element spaced from the pressure means and, during use and prior to providing the aid on a tooth, the position of the aid relative to at least a movable part of the pressure means can be set and fixed through deformation of the fastening element.

The deformable fastening element offers the possibility of adjusting the position of the aid provided on the fastening element to the position of the tooth on which the aid is to be placed, without requiring adjustment of the position of the pressure means. This provides the advantage that the pressure means can be fixedly connected with the mold, that the fastening means and the aid can then be applied and, on the basis of the dental impression, positioned in an optimum manner, whereupon the position of the aid can further be adjusted in order to achieve a desired corrective effect of the aid during use of the aids.

In further elaboration of this embodiment, each pressure means is capable of carrying at least two and preferably four dental aids. For this purpose, only a limited number of pressure means are necessary for a complete set of teeth and, moreover, aids can simultaneously be provided on both the upper teeth and the lower teeth. The fastening element being deformable, and position of each aid can be adjusted relative to the pressure means as well as to any other aid mounted on the pressure means. The limited number of pressure means enables a compact and relatively cheap manner of construction, while as a result, the apparatus is moreover little susceptible to trouble.

In a particularly advantageous embodiment of the apparatus according to the invention, the pressure means substantially extend on the side of a tooth fastening face of a dental aid connected therewith, the arrangement being such that when the mold is positioned between two rows of teeth of a set of teeth, the pressure means are located between and each dental aid is located in front of the relevant teeth with the tooth fastening face facing the associated tooth.

Because the pressure means are located between the upper teeth and the lower teeth when the aids are placed on the teeth, the apparatus according to the invention occupies only minimum space, while the aids remain readily accessible. To the dental technician who is to bring the aids into the proper position, this has the advantage that he can determine and adjust the position of the aids in an efficient manner. To the patient in whom the aids are to be positioned, this has the advantage that positioning of the apparatus in his mouth causes relatively little inconvenience. Moreover, the chances of undesired changes of position of the apparatus inside the mouth, for instances due to pressure by lips, cheeks or tongue thereon, are significantly reduced, and the apparatus and in particular the aids remain readily accessible to the orthodontist or his assistants.

In an advantageous embodiment of the apparatus according to the invention, the pressure means comprise a displaceable plunger that is controllably accommodated in a housing connected with the mold and that is capable of carrying the dental aid. In order to prevent rotation of the positioning of the plunger-carried dental aid during the displacement of the plunger, it is preferred that the plunger has a cross section deviating from a circular form.

Another possibility for carrying and displacing the dental aid is obtained if, in accordance with a further embodiment of the invention, a diaphragm is provided in a recess for forcing out the dental aid, which diaphragm is capable of carrying the dental aid and can be displaced in the direction of pressure by the pressure means.

In order to effect a displacement, and more in particular a simultaneous displacement of a number of dental aids, in accordance with a further embodiment of the invention, it is preferred that the pressure means can be activated pneumatically or hydraulically, while, in the presence of more than one recess, a main channel is present that simultaneously supplies a control fluid to all recesses present. When a separate displacement of the various dental aids is intended, it may be preferred that the pressure means can be activated mechanically, for instance by extending the plungers outside the mold or by a pin that can be inserted into an opening in the mold to deform a diaphragm for forcing out the dental aid. Obviously, a mechanical activation of the pressure means can also be applied for forcing out all dental aids simultaneously.

The invention also relates to a method for providing a number of dental aids.

According to the invention, the method that is suitable for providing a series of dental aids on at least a number of teeth of at least one row of teeth comprises the following steps:

Forming a mold over the or each row of teeth;

forming, by means of the mold, a model of the relevant part of the set of teeth of the patient to be treated;

positioning a carrying brace near the model, whereby a number of carriers corresponding to the number of aids are connected with the carrying brace via pressure means, and whereby the carrying brace rests on at least a part of the teeth;

determining the positions of the aids to be provided on the teeth and temporarily positioning the aids relative to the model by means of the carriers and pressure means;

temporarily fixing the position of the aids in a position withdrawn from the teeth of the model;

positioning the carrying brace with the aids over at least a part of the set of teeth to be treated;

providing the aids with a fastening means such as cement;

pressing the aids against the relevant teeth by means of the pressure means so that the aids are fixedly connected with the teeth by the fastening means; and removing the brace with the carriers and pressure means, whereby at least a series of pressure and carrying means remain connected with the carrying brace when the method is carried out and can be positioned and removed from the set of teeth and/or the model in one operation.

The method according to the invention offers the advantage that it is considerably simpler than the known method and that the skills necessary for carrying out the method require a less high degree of craftsmanship than the known method. Moreover, because the aids are processed in groups, a considerable amount of time is saved when they are positioned, which has a favourable influence on the costs of the method.

Hereinafter, the apparatus and method according to the invention will be further clarified and explained with reference to the exemplary embodiments shown in the drawings. In these drawings.

Figure 1:
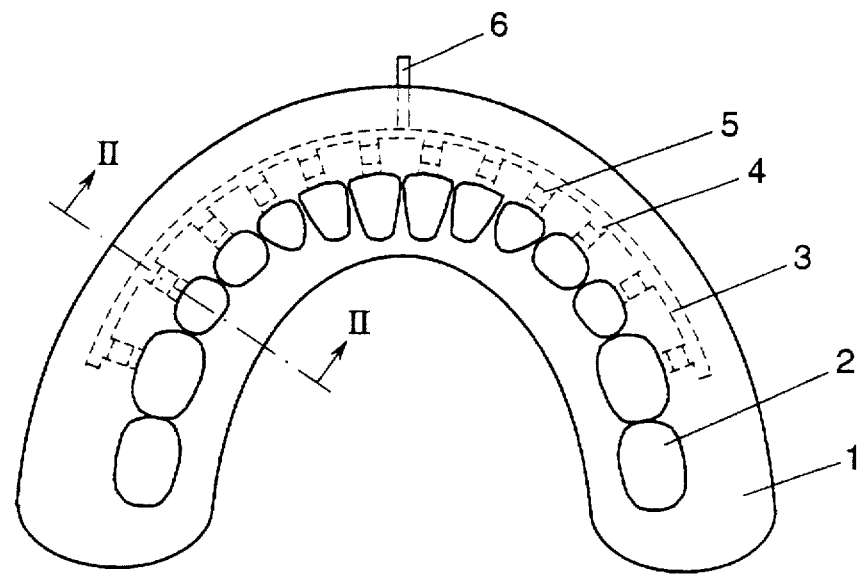
FIG. 1 is a top plan view of an apparatus according to the invention.

FIG. 1 shows a mold 1 from the side from which the impressions 2 of a row of teeth are visible. Provided in the mold 1, is conformity with the arcuate shape of the impressions 2 of the row of teeth, in a channel 3 for guiding a fluid under pressure. From most of the impressions 2 of the teeth, a recess 4 is provided leading to the channel 3, each recess 4 accommodating a plunger 5 in a guided and controlled manner. The recess 4 and the plunger 5 have corresponding, unround cross-sections so as to prevent rotation of the plunger 5 in the recess 4. Via a connecting stub 6, the channel 3 can be connected with a source of fluid under pressure, not shown.

Figure 2:
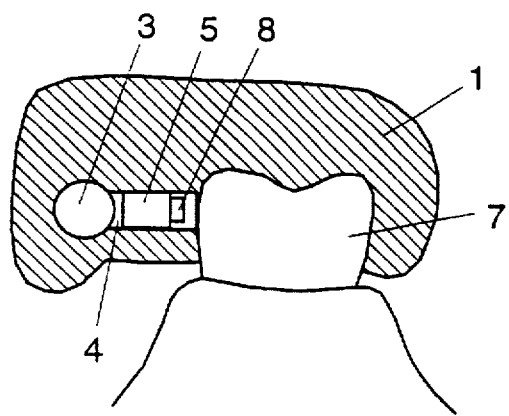
FIG. 2 shows, on an enlarged scale, a section taken on the line II—II in FIG. 1 in a position placed on a tooth.

FIG. 2 shows, in section and on an enlarged scale, the mold 1 according to FIG. 1 in a position placed on a tooth 7. As further appears from FIG. 2, the lunger 5 carries a dental aid 8, such as a bracket.

For manufacturing the mold 1, one may generally proceed as shown in for instance U.S. Pat. No. 3,738,005, i.e. first an impression is made of a row of teeth of a patient to be treated, whereupon, by means of that impression, a cast is made of the row of teeth. On this case, the positions of the dental aids to be provided on the teeth are determined, and subsequently, these dental aids are temporarily mounted on that can, whereupon the mold is formed thereon. To arrive at the apparatus according to the invention, the channel 3, the recesses 4 and the plungers 5 should be provided in the mold 1. This can be effected in several manners. For instance, a array of recesses 4 and channel 3 can be provided on the dental aids 8, after which the mold 1 is formed around it. In addition, it is also possible to provide the channel and the recesses afterwards in a mold manufactured in the known manner.

After the manufacture of the mold 1 on the cast, the mold is pulled from the cast, whereby the temporary bond between the cast and the dental aid 8 is broken, causing the latter to stay behind in the mold. The mold 1 is now ready for use, i.e. after the application of adhesive to the dental aids 8 the mold 1 can be slid over the row of teeth of the patient. In this respect, it should be observed that a dental aid 8 having bonding agent applied thereto is inwardly receded in the mold 1 relative to the impression 2 of a tooth, as shown in FIG. 2. Such withdrawn position can be obtained by mounting the dental aid on the cast accordingly, i.e. by choosing a greater thickness for the temporary bond on the cast than for the bonding agent on the tooth 7. In this manner, the mold 1 can be slid on the row of teeth from above without the tooth 7 (prematurely) contacting the bonding agent.

After the mold 1 has thus been positioned on the row of teeth, a fluid is supplied under pressure, for instance air, to the channel 3 via the stub 6. Because this channel is in open communication with all recesses 4, the plungers 5 present in those recesses will be urged in the direction of the impressions 2 of the row of teeth. Together with the plungers 5, the dental aids 8 carried by then are displaced, causing the bonding agent on each dental aid to contact the tooth 7. Due to this movement perpendicular to the tooth 7, the air that is first present between the bonding agent and the tooth 7 is forced out sideways, while that movement also provides that the dental aid 8 is optimally pressed against the tooth 7. The fluid in the channel 3 and in the recesses 4 is held under pressure until the bonding agent has sufficiently cured and the dental aids 8 are firmly secured to the row of teeth. After this, the mold 1 is removed and the treatment for the purpose of which the dental aids had to be provided on the row of teeth can be started.

Figure 3:
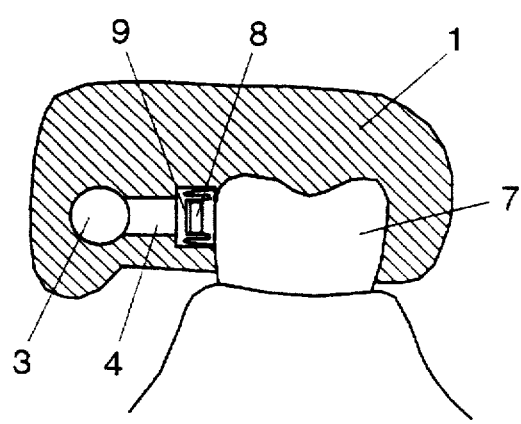
FIG. 3 shows a modified embodiment in a manner corresponding to that of FIG. 2.

FIG. 3 shows a structural variant in the manner of FIG. 2, wherein the plunger is replaced by a diaphragm 9 having a flat central portion and a bellows-shaped outer-circumferential area. The flat central portion carries the dental aid 8, while the bellows-shaped outer-circumferential area permits movement in the direction of the tooth 7 when fluid is supplied under pressure via the channel 3 and the recess 4.

Figure 4:
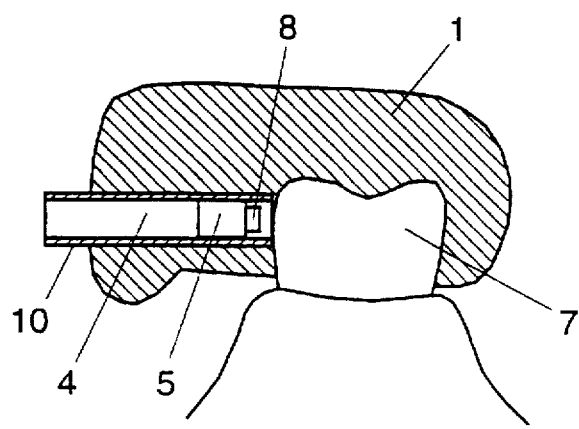
FIG. 4 shows a further modified embodiment in a manner corresponding to that of FIG. 2.

FIG. 4 shows a structural variant in the manner of FIG. 2, wherein the channel 3 in the mold 1 is left out and the recesses are surrounded by a sleeve part 10 extending outside the mold 1. By coupling a hose, not shown, to the sleeve part 10 and connecting it with a source for fluid under pressure, the plunger 5 carrying a dental aid 8 can be controllably displaced in the above-described manner to enable mounting the dental aid 8 on the tooth 7.

Figure 5:
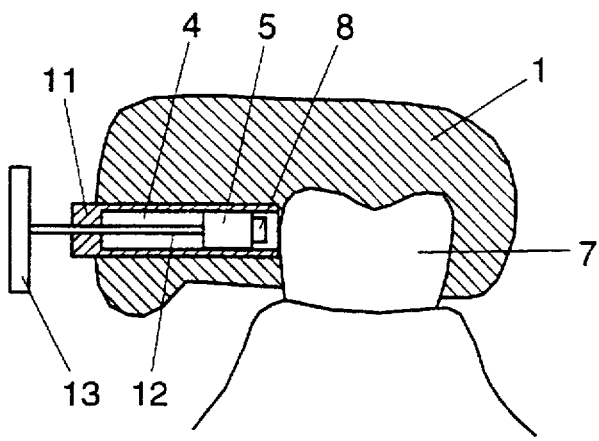
FIG. 5 shows an alternative embodiment in a manner corresponding to that of FIG. 2.

FIG. 5 shows a further structural variant in the manner of FIG. 2, wherein provisions are made for enabling mechanical displacement of the plunger 5. For that purpose, the air channel 3 is left out and the recess 4 is surrounded by a cylindrical sleeve 11 extending outside the mold 1, where it has a bottom with a bore forming a guide for a pin 12, of which pin 12 one end abuts against the plunger 5 and the other end comprises a push button 13. After the mold 1 has been provided on the row of teeth, as discussed hereinabove, the dental aid 8 with bonding agent can be mounted on the tooth 7 by pushing the button 13 by mechanical means.

Figure 6:
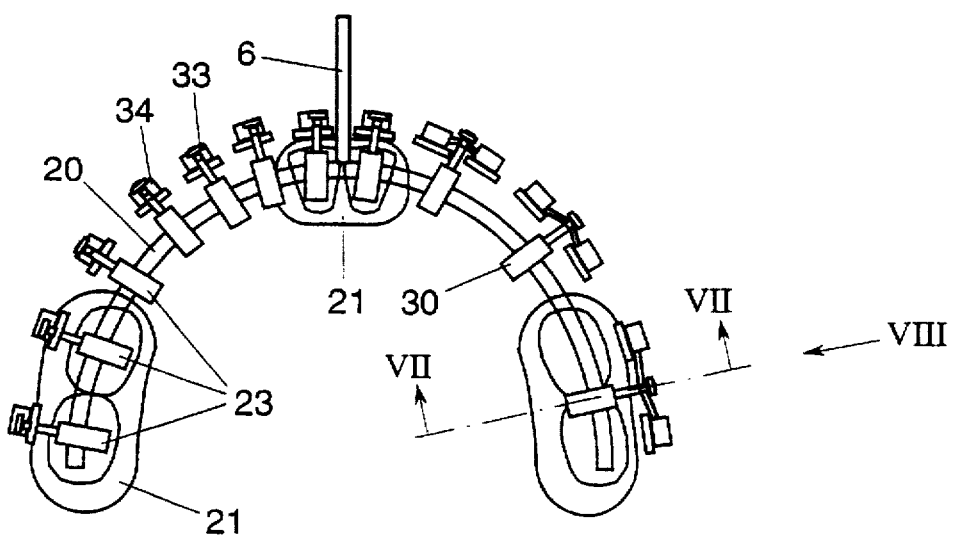
FIG. 6 is a partly sectional top plan view of an alternative embodiment of an apparatus according to the invention.

FIG. 6 shows an alternative embodiment. In this embodiment, a brace 20, bent in the shape of a dental arch, is on three places provided with a mold part 21, in which mold on three places provided with a mold part 21, in which mold parts 21 at least an impression of a part of a number of upper teeth and a part of a number of lower teeth is provided. These dental impressions are obtained in a known manner as described hereinabove. As a matter of fact, the mold 21 can also be of a one-piece design in accordance with that above-described method, with the brace being incorporated into the mold.

Figure 7:
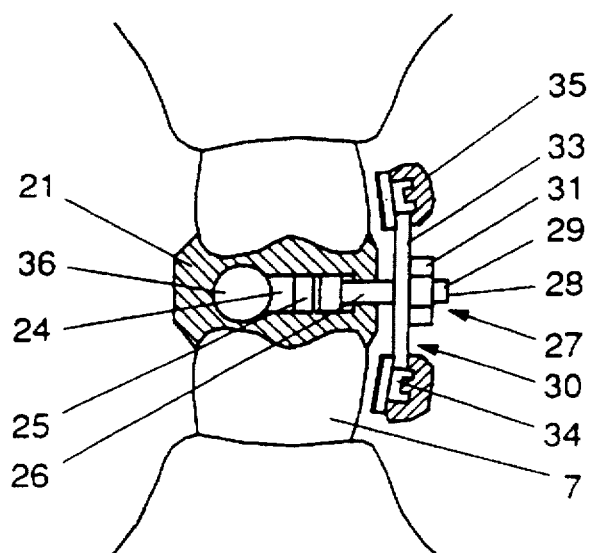
FIG. 7 shows, on an enlarged scale, a section taken on the line VII—VII in FIG. 6 in a position placed on a tooth.

Provided on the brace are a number of pressure means 23, each of which comprises a pressure cylinder 24 including a controllable piston 25, as shown in FIG. 7. Extending from the controllable piston 25, as shown in FIG. 7. Extending from the piston 25 outside the pressure cylinder 24 is a piston rod 26. The part 27 extending outside the pressure cylinder 2 is provided with an axial cut 28 and external screw thread 29. Into the cut 28, a fastening element 30 is slid, whereupon the fastening element 30 is secured in the cut, and accordingly on the piston rod 26, with a nut 31 tightened on the external screw thread.

Figure 8:
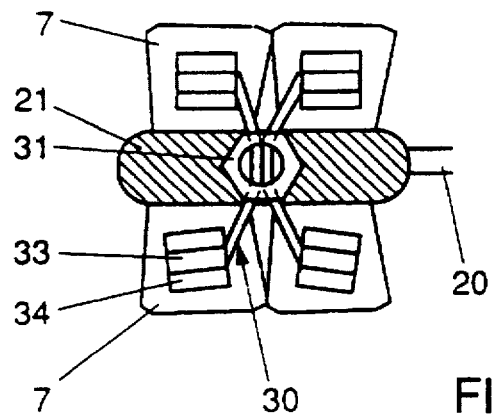
FIG. 8 shows a part of the apparatus according to FIG. 6 in front view according to the arrow VIII in FIG. 6.

As shown in the right-hand part of FIG. 6, the fastening element 30 consists of two deformable wire sections 32 of rectangular cross section, which wires, when positioned alongside one another, fit exactly into the width of the cut 28. The ends 33 extending outside the piston rod 26 are bent to enable a dental aid, in this case a bracket 34, to be mounted thereon, for instance by means of a bonding agent 35. By changing the bend of the end 33, the position of the bracket can be optimized, as appears from the different positions of the brackets as shown in FIG. 8. The wire sections 30 are rigid so that they can be deformed by means of, for instance, pliers, but cannot be bent by the pressure force that can be produced by the pressure device. Preferably, they have a rectangular cross sectional, the widest side extending at right angles to the direction of pressure.

The pressure means 23 as shown on the left-hand side of FIG. 6 comprise fastening elements having only one wire section on which only two aids are mounted.

Extending through or along the brace 20 is a central air channel 36 that is connectable to a pressure source not shown. Through the supply of air to the pressure means, the pistons 25 of the different pressure means 23 can be moved in a controlled manner, as has been discussed at length in respect of the first embodiment (FIGS. 1–5).

The fastening element enables mounting the pressure means in fixed positions on the brace, while it is nevertheless possible to simultaneously provide both upper teeth and lower teeth with aids such as brackets, permitting optimization of the position of each individual aid.

The pressure means according to FIGS. 6–8 are designed as means operating on partial vacuum, so that when the aids are being positioned on the teeth, the fastening element 30 is moved in the direction of the cylinder housing and the brace. As a result, the aids are as it were pulled against the teeth.

Figure 9:
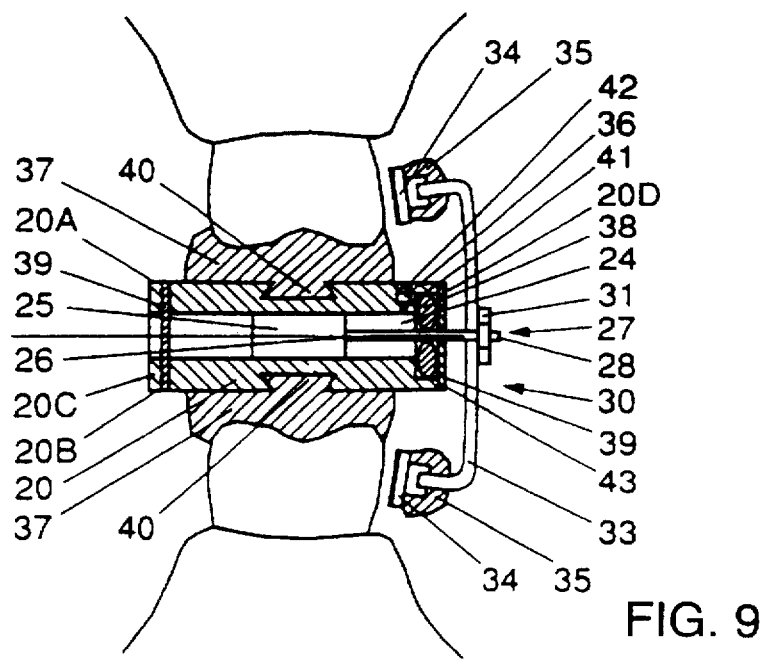
FIG. 9 shows a similar sectional view as shown in FIG. 7 of another exemplary embodiment according to the invention.

FIG. 9 shows a similar sectional view as shown in FIG. 7 of another embodiment according to the invention. Here, the brace 20 is made from solid material, the pressure means 23 being formed by bores 24 in the solid brace material wherein pistons 25 are located. The upwards and downwards facing surfaces 20A, 20B of the brace 20 are provided with trapezoidal recesses 40 capable of receiving modelling material 37, which modelling material 37 is given a shape matching the set of teeth that is to be treated. Hence through removal of the modelling material 37, the brace 20 can readily be used for sets of teeth of different patients without requiring a elaborate operations for manufacturing a mold. In the upper surface 20A of the brace 20, a groove is cut forming the air channel 36. In the groove, ducts 41 have been drilled to each chamber 24 which put the air channel 36 into communication with the chamber 24. Next, the air channel 36 is closed off with a closing strip 42. Obviously, the air channel 36 is connectable to a pressure means source (not shown). The duct 41 terminates in the cylinder 24 at such a location that under the influence of excess pressure in the channel 36, the piston 25 moves to the left and the brackets 34 are pressed against the teeth or molars. The chamber 24 extends throughout the width of the brace 20. Provided at the convex side 20D of the brace 20 is a chamber 39 serving to accommodate an O-ring 38. The O-ring 38 not only closes off the chamber 24 relative to the atmosphere, the O-ring 38 moreover centers and guides the piston rod 26. To prevent the piston 25 from being blown out of the chamber 24 unexpectedly, for instance in the absence of the fastening element 30, a locking pin 44 is positioned at the concave side 20C of the chamber 24 after the piston 25 has been slid into the chamber 24. The O-ring 38 is secured in the O-ring chamber 39 by a cover 43.

When the pressure means are constructed in the manner as shown in FIGS. 6–9, the brace and in particular the pressure means can be positioned between the upper and lower teeth of a patient when the aids are being positioned. This has the important advantage that it enables a far more compact construction, which prevents unnecessary inconvenience to the patient when the apparatus is positioned and held in his mouth and when the aids are positioned. Moreover, the aids remain more easily and suitably accessible to the orthodontist or his assistants, enabling better and more precise positioning.

With an invention according to the invention, it is pre-eminently possible to position and fix the different aids on the mold outside the patient's mouth and to subsequently provide the aids on the patient's teeth through joint energization of all pressure means at the same time.

In an embodiment according to FIGS. 6–8, braces 20 are supplied in a number of sizes, preferably three, which braces render the apparatus suitable for any mouth. After all, the fastening means enable any further correction.

It will be readily understood that many modifications and variants are possible within the scope of the invention. For instance, the diaphragm 9 as used in FIG. 3 may also be operated by means of a hose to be connected, as shown in FIG. 4, or by a pin 12 having a push button 13, as shown in FIG. 5. Instead of manually, the push button 13 may also be pressed mechanically, for instance by means of a cam disk whose rotation is coupled to a number of further cam disks, permitting simultaneous operation of all push buttons.

The diaphragm can be formed or moved by a part of the outside of a hose disposed transversely behind the aid or of a balloon disposed behind the aid. The fastening element 30 can be formed by other means, such as for instance a sheet-shaped part or a molded piece, and a different number of dental aids can be provided on one pressure means.

Further, it is possible to fixedly connect the dental aids with the pressure means, the pressure means being connected with a number of dental braces 20 such that the position of the different pressure means relative to each other and relative to the braces and mold can be adjusted, so that for each pressure means the desired direction of pressure can be selected.

I claim:

1. An apparatus for providing dental aids on a plurality of teeth of at least one row of teeth, said apparatus comprising:

a mold containing an impression of at least a portion of the teeth from a row of teeth;

a series of pressure means being connected to the mold and provided with fastening means for connecting each dental aid to the series of pressure means, where the series of pressure means are adapted to move each dental aid in a controlled manner from a first position to a second position; and means for connecting the series of pressure means to a pressure means supply means such that the series of pressure means are activated to at least several of ether by the pressure medium.

2. An apparatus according to claim 1, wherein the fastening means comprises at least a deformable fastening element that is fixedly connectable with the pressure means, while at least one of the dental aids are positioned on the fastening element spaced from the pressure means and, during use and prior to providing aid on a tooth, a position of the aid relative to at least a movable part of the pressure means are set and fixed through deformation of the fastening element.

3. An apparatus according to claim 2, wherein each pressure means is capable of carrying at least two dental aids.

4. An apparatus according to claim 2, wherein each of said dental aids has a tooth fastening face, where the pressure means extend substantially on a side of said tooth fastening face an arrangement being such that when the mold is positioned between two rows of teeth of a set of teeth the pressure means are located between and each dental aid is located in front of relevant teeth and where the tooth fastening face faces the associated tooth.

5. An apparatus according to claim 4, wherein the pressure means comprises a plunger which is displaceable through creation of partial vacuum.

6. An apparatus according to claim 1, wherein the pressure means comprises a diaphragm capable of carrying the dental aid.

7. An apparatus according to claim 1, wherein the pressure means are connected with a brace that is bent in accordance with a dental arch and that is fixedly connected with the mold, a direction of movement of each pressure means being substantially in a plane of the brace and extending approximately at right angles to the brace.

8. An apparatus according to claim 1, wherein the pressure means are activated pneumatically or hydraulically, while a main channel is present that simultaneously supplies an operating fluid to all pressure means present.

9. A method for providing a series of dental aids on at least a plurality of teeth of at least one row of teeth, comprising the following steps:

forming a mold over each row of teeth;

forming, by means of the mold, a model of a relevant part of the set of teeth of a patient to be treated;

positioning a carrying brace near the model, whereby a plurality of carrier corresponding to the number of aids are connected with a carrying brace via pressure means, and whereby the carrying brace rests on at least a part of the teeth;

determining positions of the aids to be provided on the teeth and temporarily positioning the aids relative to the model by means of the carriers and pressure means;

temporarily fixing the position of the aids in a position withdrawn from the teeth of the model;

positioning the carrying brace with the aids over at least a part of the set of teeth to be treated;

providing the aids with a fastening means including cement;

pressing the aids against the relevant teeth by means of the pressure means so that the aids are fixedly connected with the teeth by the fastening means; and removing the carrying brace with the carriers and pressure means, whereby at least a series of pressure and carrying means remain connected with the carrying brace when the method is carried out and are positioned and removed from the set of teeth and/or the model substantially simultaneously.

* * * * *

UNITED STATES PATENT AND TRADEMARK OFFICE
CERTIFICATE OF CORRECTION

PATENT NO. : 5,791,896

DATED : AUGUST 11, 1998

INVENTOR(S) : IPENBURG

It is certified that error appears in the above-identified patent and that said Letters Patent is hereby corrected as shown below:

Col. 1, line 40: "out" should read --cut--

Col. 4, line 1: "Forming" should read --forming--

Col. 5, line 12: "can" should read --cast--

Col. 6, line 32: "2" should read --24--

Col. 8, line 24: "means supply" should read --medium supply--

Col. 8, line 24: insert --at least several of-- after "that"

Col. 8, line 25: "to at least several of ether" should read --together--

Signed and Sealed this

Fourteenth Day of December, 1999

Attest:

Q. TODD DICKINSON

*Attesting Officer*   Acting Commissioner of Patents and Trademarks